US008012709B2

(12) United States Patent
Verheijen et al.

(10) Patent No.: US 8,012,709 B2
(45) Date of Patent: Sep. 6, 2011

(54) METHOD FOR DETERMINING IF A SUBJECT HAVING TYPE II DIABETES HAS A KIDNEY DISORDER

(75) Inventors: Johan Hendrikus Verheijen, TX Berkel en Rodenrijs (NL); Jan Roeland Occo Hanemaaijer, NP Voorhout (NL); Michaela Diamant, GW Muiderberg (NL)

(73) Assignees: Nederlandse Organisatie voor Toegepast-Natuurwetenschappelijk Onderzoek, Delft (NL); Leids Universitair Medisch Centrum, Leiden (NL)

( * ) Notice: Subject to any disclaimer, the term of this patent is extended or adjusted under 35 U.S.C. 154(b) by 76 days.

(21) Appl. No.: 12/340,994

(22) Filed: Dec. 22, 2008

(65) Prior Publication Data

US 2009/0117604 A1    May 7, 2009

Related U.S. Application Data

(62) Division of application No. 10/276,520, filed as application No. PCT/NL01/00373 on May 17, 2001, now Pat. No. 7,482,135.

(30) Foreign Application Priority Data

May 17, 2000    (EP) .................................... 00201755

(51) Int. Cl.
*C12Q 1/37* (2006.01)
(52) U.S. Cl. ........... 435/23; 435/183; 435/195; 435/219
(58) Field of Classification Search .................... 435/23, 435/183, 195, 219
See application file for complete search history.

(56) References Cited

U.S. PATENT DOCUMENTS

| 5,736,341 A * | 4/1998 | Sorsa et al. ..................... 435/7.1 |
| 2010/0068151 A1 * | 3/2010 | Rosenblum et al. ......... 424/9.34 |

FOREIGN PATENT DOCUMENTS

| EP | 0 691 409 | 1/1996 |
| EP | 0 985 932 | 3/2000 |
| EP | 1 004 674 | 5/2000 |
| WO | WO 97/38314 | 10/1997 |
| WO | WO 97/40157 | 10/1997 |
| WO | WO 97/41441 | 11/1997 |

OTHER PUBLICATIONS

Sommerville et al. Genome Biology (2003) 4:216.*
Zijl et al. Clinical Biochemistry (2010) 43: 635-639.*
Diamantt, M. et al, Elevated matrix metalloproteinase-2 and -9 in urine, but not in serum, are markers of Type 1 diabetic nephropathy, 2001, Letters, Diabetes Medicine, pp. 423-426, vol. 18, Diabetes UK.
Lenz, Oliver et al, Matrix Metalloproteinases in Renal Development and Disease, 2000, pp. 574-581, Journal of the American Society of Nephrology, vol. 11, American Society of Nephrology.
Shiau, Ming-Yuh et al, Increased Circulatory MMP-2 and MMP-9 Levels and Activities in Patients with Type 1 Diabetes Mellitus, Nov. 2006, The Mount Sinai Journal of Medicine, vol. 73, No. 7.
Tashiro, Kyoichi et al, Levels of Urinary Matrix MetaUoproteinase-9 (MMP-9) and Renal Injuries in Patients With Type 2 Diabetic Nephropathy, 2004, Journal of Clinical Laboratory Analysis, pp. 206-210, vol. 18, Wiley-Liss, Inc.
A. Pagenstecher et al., "RNAse protection assays for the simultaneous and semiquantitative analysis of multiple murine matrix metalloproteinase (MMP) and MMP inhibitor mRNAs", Journal of Immunological Methods., vol. 206, No. 1-2, Aug. 7, 1997, pp. 1-9, XP002150385 Elsevier Science Publishers B.V.., Amsterdam., NL ISSN: 0022-1759 abstract.
Webster's II New Riverside Dictionary (1994) (Houghton-Mifflin: Boston, MA) p. 667.
Moses et al. "Increased incidence of matrix metalloproteinases in urine of cancer patients" Cancer Research (1998) 58(1395-1399).
Fukudome et al. "Peritonitis increases MMP-9 activity in peritoneal effluent from CAPD patients" Nephron (2001) 87: 35-41.
Lindblad et al. "The role of diabetes mellitus in the aetiology of renal cell cancer" Diabetologia (1999) 42: 107-112.
Thrailkill et al. "Characterization of matrix metalloproteinases in human urine: alterations during adolescence" Pediatr. Nephrol. (1999) 13: 223-229.
Ebihara et al. "Increased plasma metalloproteinase-9 concentrations precede development of microalbuminuria in Non-insulin-dependent diabetes mellitus" Am. J. Kidney Diseases (1998) 32(4): 544-550.
Macmillan et al. "Characterization of glomerular epithial cell metalloproteinase as matrix metalloproteinase-9 with enhanced expression in a model of membranous nephropathy" J. Clin. Invest. (1996) 97(4): 1094-1101.

* cited by examiner

*Primary Examiner* — Sandra Saucier
*Assistant Examiner* — Susan Hanley
(74) *Attorney, Agent, or Firm* — Young & Thompson

(57) ABSTRACT

The present invention relates to a method for determining if a subject having Type II diabetes has a kidney disorder by measuring the level of matrix metalloproteinase 8 (MMP-8) in the urine of a subject having Type II diabetes and comparing this level to a reference sample or a sample from a healthy subject and determining if the subject has a kidney disorder base on the presence of increased levels of MMP-8 in the urine compared to the reference values or reference sample.

2 Claims, 5 Drawing Sheets

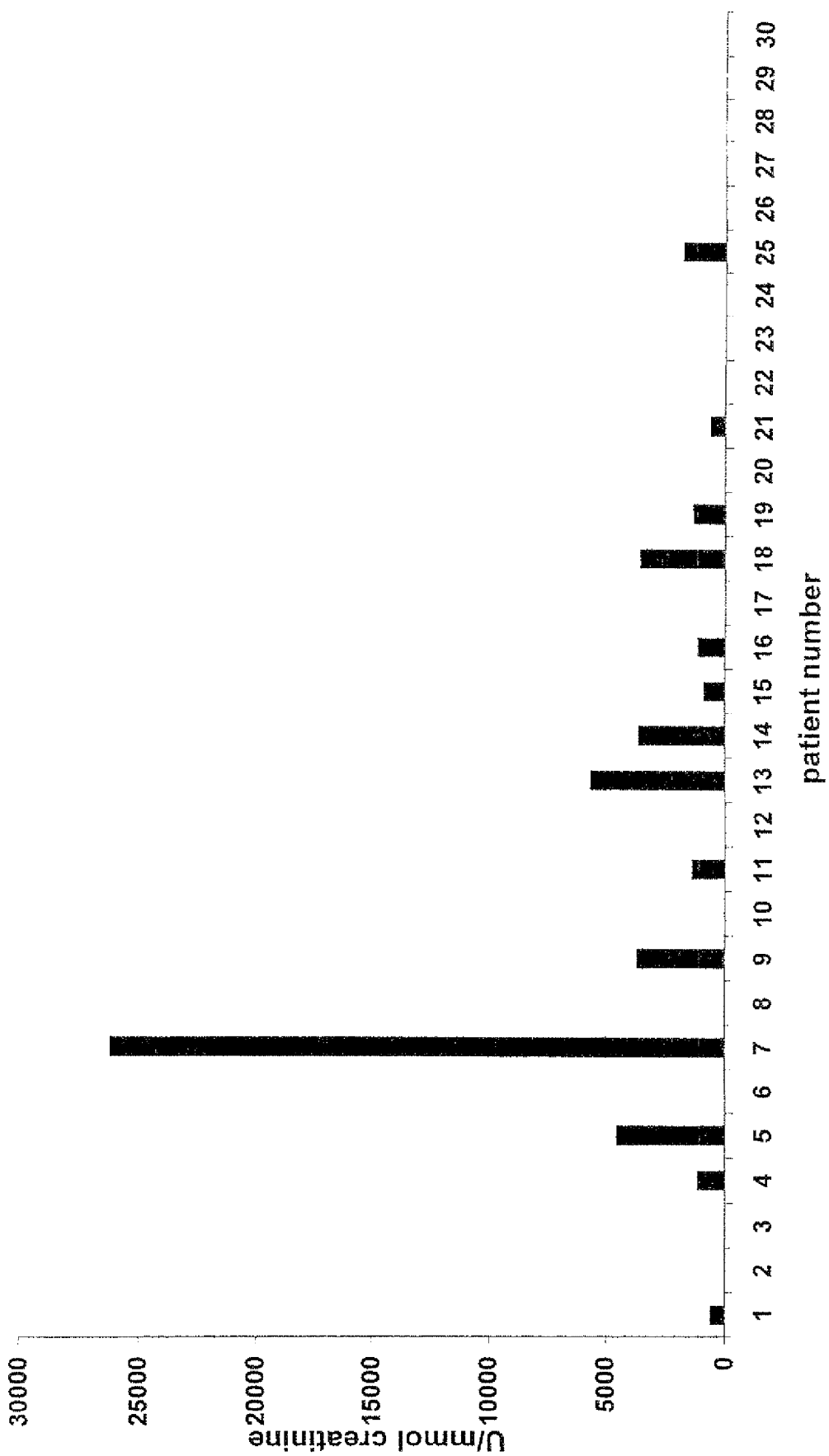

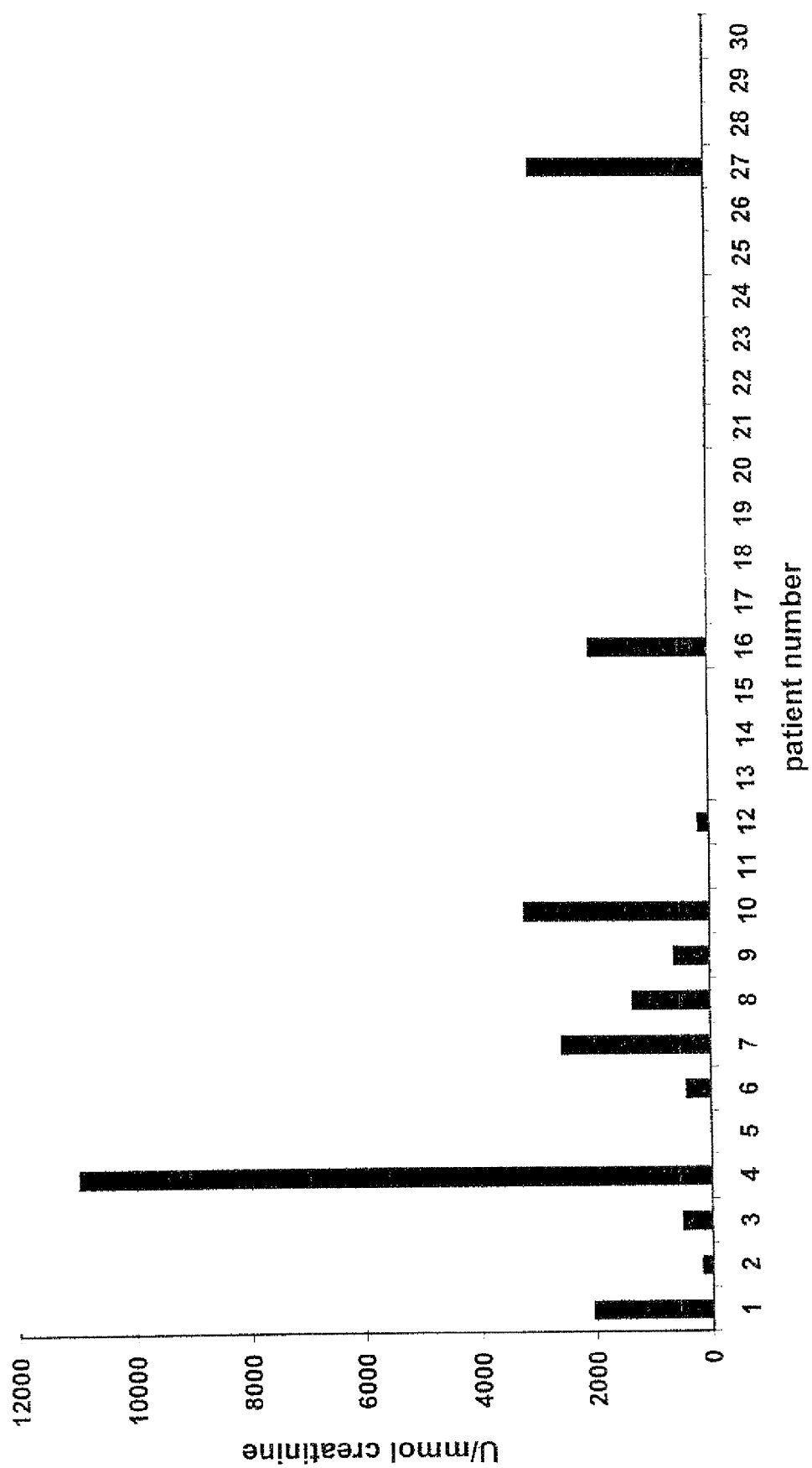

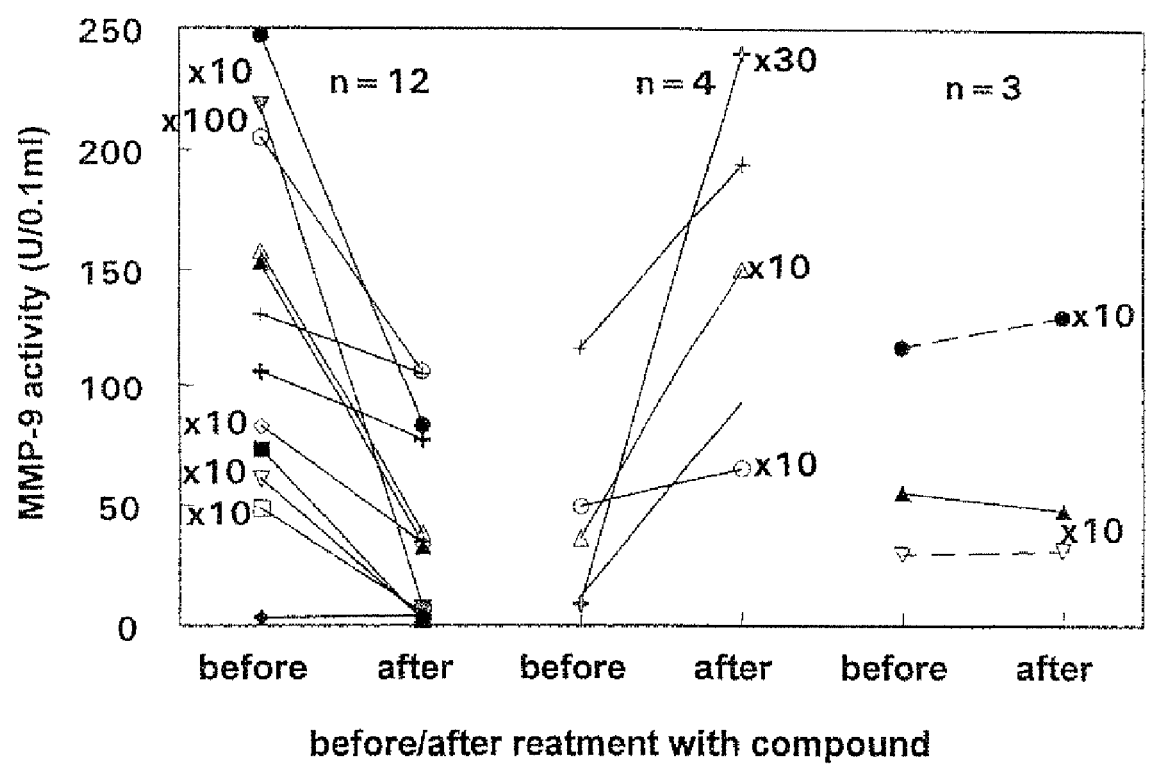

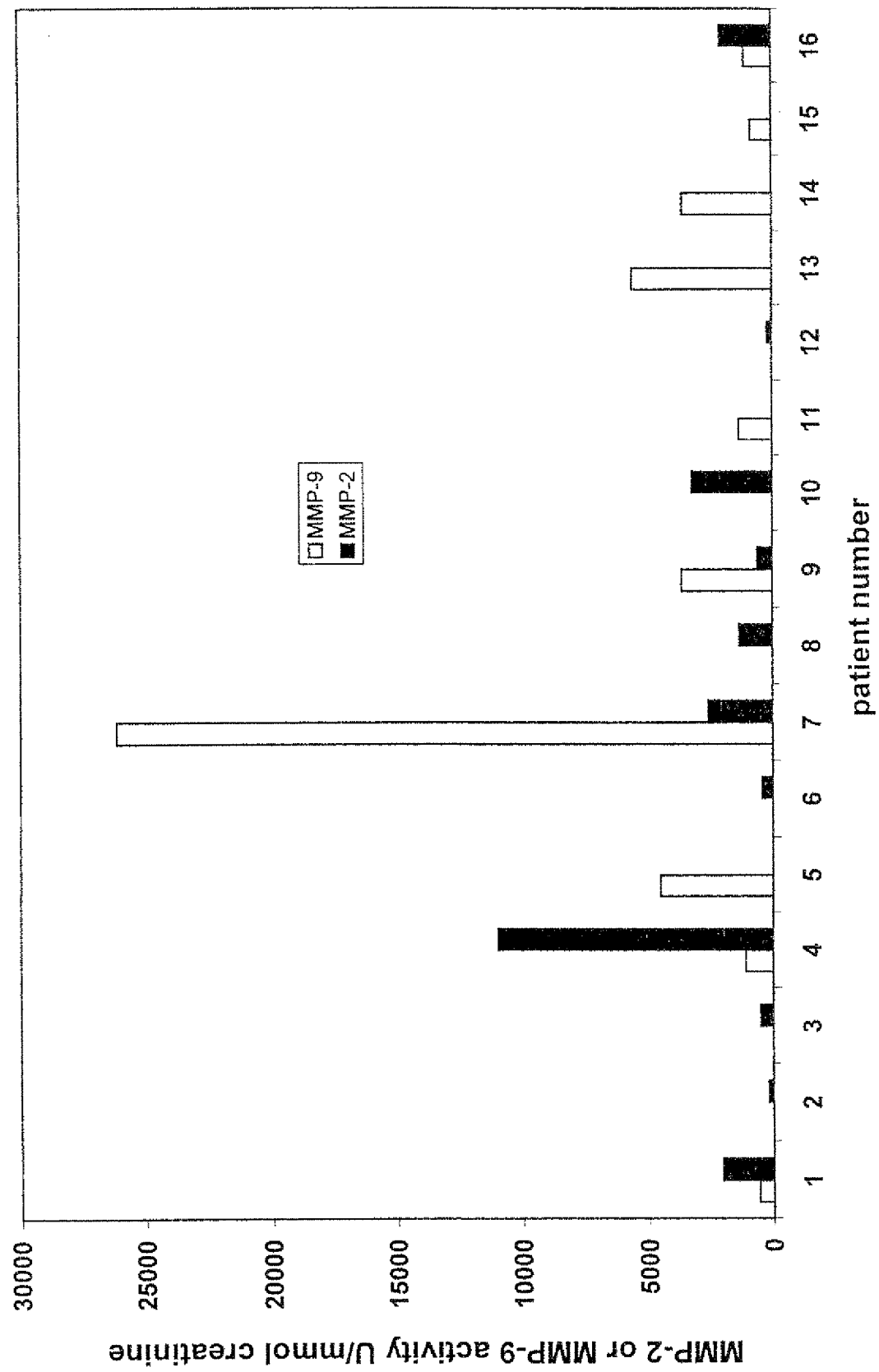

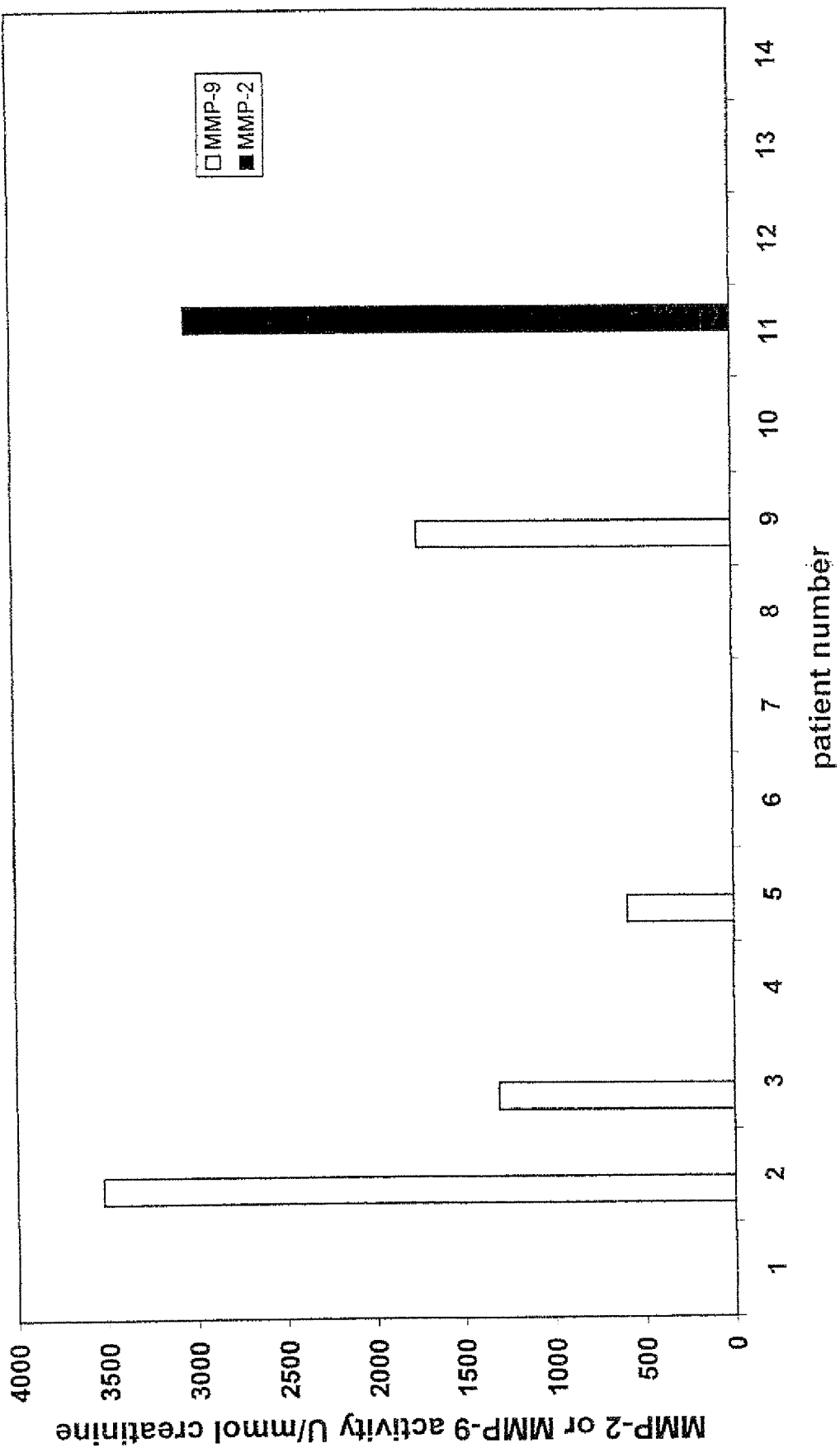

METHOD FOR DETERMINING IF A SUBJECT HAVING TYPE II DIABETES HAS A KIDNEY DISORDER

This application is a divisional application of Ser. No. 10/276,520, filed Jul. 15, 2003, now U.S. Pat. No. 7,482,135, which claims priority to PCT/NL01/00373, filed May 17, 2001, which claims priority to European Application No. 00201755.6, filed May 17, 2000. The teachings of the above applications are hereby incorporated by reference. Any disclaimer that may have occurred during prosecution of the above referenced applications is hereby expressly disclaimed.

FIELD OF THE INVENTION

This invention is in the field of methods and techniques for the prediction and/or diagnosis of renal disorders, and in particular for the prediction and/or diagnosis of renal damage associated with diabetes, and in particular with diabetes mellitus. In particular, the invention relates to a method of determining the presence and amount of a proteolytic enzyme in urine and the use thereof as diagnostic or prognostic parameter in diseases involving matrix remodelling such as diabetes.

BACKGROUND OF THE INVENTION

Increased or decreased matrix remodelling is involved in many diseases and pathological processes, including cancer, angiogenesis, restenosis, arteriosclerosis and other vascular remodelling processes, vascular complications of diabetes such as retinopathy and nephropathy. Dysregulation of remodelling processes frequently causes problems or might be even essential in the development of the particular disease. Matrix remodelling plays a key role in invasion and metastasis of tumor cells, cartilage degradation in rheumatoid arthritis and vascular remodelling. Proteolytic enzymes belonging to the plasmin-system and the matrix-metalloprotease system are main actors in the various remodelling processes. Consequently measuring these components or influencing their activity are potential targets for diagnostic or therapeutic method development.

Vascular complications and renal disease are frequent complications of e.g. diabetes mellitus. Early renal disease is accompanied by leakage of protein into the urine (microalbuminuria) which is used as a diagnostic marker for this complication. Microalbuminuria appears to be preceded by widespread endothelial dysfunction, therefore much attention has been devoted to the study of the possible use of circulating endothelium-derived molecules as markers of early stage diabetic kidney failure. Local proteolytic activity is involved in micro-vascular damage leading to kidney failure and measurement of the local level or activity of certain proteolytic enzymes or their inhibitors might be indicative of occurring damage to microvascular integrity. Some data have been presented suggesting that increased levels of matrix metalloproteases, one group of proteolytic enzymes thought to be involved in formation of vascular damage, occur in peripheral blood possibly as a representation of local levels in the kidney.

For the above, reference is inter alia made to I. Massova et al., FASEB J. 12, 1075-1095 (1998); P. Primakoff et al., Trends Genet. 16, 83-87 (2000); and B. L. Tang and W. Hong, FEBS Lett. 445, 223-225 (1999). However, none of these references discloses or suggests to determine proteolytic enzymes in urine samples.

Generally, the measurement of proteolytic enzymes in peripheral blood, serum or plasma is cumbersome, as it involves the use of blood samples, which have to be collected from the patient by a doctor or a skilled medical technician. This may put a great deal of strain on the patient, not only because of the invasive techniques required to collect the blood sample, but also because this will usually involve a visit to a clinic or a hospital. In addition blood, serum or plasma contain numerous compounds potentially interfering with the measurement of proteolytic enzymes requiring carefully developed procedures which are prone to complications. In urine hardly any interfering substances occur, thus making reliable measurement of proteases much more simple.

Lenz et al., Journal of the American Society of Nephrology, March 2000, Vol. 11, No. 3 review the role of matrix metalloproteinases in renal development and disease, including non-inflammatory glomerular diseases such as diabetic nephropathy.

However, in doing so, Lenz et al. refer either to in vitro studies involving the measurement of MMP-expression and -activity at the cellular level (e.g. in mesangial cells), to studies involving the use of kidney biopsies, or to studies involving the measurement of expression of MMP-encoding mRNAs. Thus, this reference does not suggest to measure MMPs in urine, and also does not teach that the levels of proteolytic enzymes in urine can be used as diagnostic markers for (early) kidney damage associated with diabetes (mellitus).

Furthermore, with reference to the studies mentioned in their review, Lenz et al. teach that, contrary to inflammatory glomerular diseases such as glomerulonephritis, which are generally associated with increased expression and activity of MMPs, MMP-expression and MMP-activity are in fact decreased in non-inflammatory glomerular diseases such as diabetic nephropathy. In this respect, it should be noted that according to the invention, early renal damage associated with diabetes was found to be associated with a marked increase in the levels/activity of—for example—MMP-2 and MMP-9 in urine.

Senatorksi et al., Res. Exp. Med (Berl) 1998 December; 198 (4):199-206, describe a study in which urine activity of cathepsin B and collagenase as well as urine excretion of TGF-β1 and fibronectin were measured in patients suffering from membranous glomerulonephritis.

However, as stated in the first paragraph of the section entitled "Materials and methods" on page 201, this study specifically excluded patients with diabetes. Thus, this reference teaches the skilled person nothing on the levels of proteolytic enzymes in the urine of patients suffering from diabetes. In particular, this reference does not teach that the levels of proteolytic enzymes in the urine of a diabetes patient can be used as diagnostic markers for (early) kidney damage.

In addition, Senatorksi et al. generally refer to the measurement of "collagenases" in urine, in which the term "collagenases" is apparently used generically to indicate any and all enzymes from the (very extensive) entire group/family of enzymes that may degrade native collagen. This is confirmed by the fact that the fluorometric technique used by Senatorksi to determine said "collagenases" is not very specific (e.g. for individual collagenases or MMPs).

Also, two of the most important markers in urine used according to the present invention, MMP-2 and MMP-9, are not "collagenases" but "gelatinases" (compare the discussion of MMP-2 and MMP-9 in the review article by Lenz et al., mentioned above).

In the invention, it has now been found that the presence and/or the levels of certain proteases in the urine of a subject may be used as a diagnostic and/or prognostic parameter for renal disorders, and in particular for (early) renal damage associated with diabetes mellitus.

In particular, in the invention, it has been found that the presence and/or the levels of certain proteases in urine may be indicative for renal damage which is not—or not yet—detectable by the known method of determining the leakage of protein in the urine. Thus, the method of the invention is not only more reliable than determining (the extent of) microalbuminuria, but may also provide valuable information to the clinician even before any damage to the kidneys has already progressed to such a stage that microalbuminuria occurs.

Also, in the invention, it has surprisingly been found that the presence and/or the levels of said proteases in urine may be used as reliable markers for (early) renal damage which is not—or not yet—detectable by increased levels of matrix metalloproteases in peripheral blood. Thus, besides putting less strain on the patient and generally being more convenient, the method of the invention is also more reliable than measuring the amount of proteases in blood or plasma, allowing for earlier detection of possible renal damage, in particular in diabetic patients.

It should however be noted that the invention is not limited to (early) detection of renal damage in diabetes or other diseases with kidney failure as complication, but can also be employed for monitoring or diagnosis of remodelling of the peritoneal membrane. Remodelling of the peritoneal membrane is a frequent problem in patients undergoing continuous ambulatory peritoneal dialysis (CAPD). For instance, one of the further (non-limiting) applications of the invention that is envisaged is to monitor adequacy of dialysis in such patients.

SUMMARY OF THE INVENTION

The invention provides a method of using the determination of one or more proteases alone or in combination, in urine as a sensitive diagnostic or prognostic marker for early kidney damage as e.g. often occurring as a complication of diabetes mellitus. Said proteases could belong to the group of matrix metalloproteases or related enzymes such as ADAMS or ADAMTS but also certain serine-, cysteine- or aspartyl-proteases could be used. Furthermore said proteases might be fragments of originally larger proteins, complexes of proteins, or even soluble fragments of normally insoluble, membrane bound, enzymes which are still recognizable either by remaining enzymatic activity or antigenic determinants. Urine is a very convenient medium—since it normally contains no or extremely low levels of proteolytic enzymes—which is frequently used in current diagnostic methods for diabetes or diabetic nephropathy like glucose level, or albumin or protein level and thus fits well with current clinical routine practice.

Thus, in a first aspect, the invention relates to a method for determining whether a urine sample has been obtained from a subject suffering from a kidney disorder and/or from kidney damage, said method comprising the steps of:
a) providing at least one urine sample from said subject;
b) determining in said at least one urine sample the presence and/or the level of at least one proteolytic enzyme; and optionally comprising the further step of:
c) comparing one or more of the values determined in step b) with at least one reference value or reference sample.

The invention also relates to a method for detecting and/or monitoring (early) kidney damage and/or kidney disorders in a patient, comprising steps a) to c) above.

In particular, the urine sample provided in step a) may be a sample collected from a patient/individual who is judged to be at risk of—and/or who is suspected to suffer from—a kidney disorder and/or kidney damage; or more generally from a patient that suffers from a condition or disorder that may cause and/or that is associated with kidney disorders and/or kidney damage or an increased risk therefor (e.g. as a complication of said condition or disorder).

More in particular, the urine sample provided in step a) may be a sample collected from a patient/individual who is judged to be at risk of—and/or who is suspected to suffer from—kidney damage caused by and/or associated with diabetes; or more generally may be a sample collected from a patient suffering from diabetes.

Even more in particular, the urine sample provided in step a) may be a sample collected from a patient/individual who is at risk of—and/or who is suspected to suffer from—kidney damage caused by and/or associated with diabetes mellitus type 1 and/or diabetes mellitus type 2; or more generally may be a sample collected from a patient suffering from diabetes mellitus type 1 and/or diabetes mellitus type 2.

However, the invention may also be applied to urine samples that have been obtained from patients that are suffering from and/or suspected to suffer from other disorders that may lead to renal damage (including but not limited to microalbuminuria) or an increased risk thereof, including but not limited to disorders such as (auto) immune mediated glomerulonephritis, amyloidosis, nephrotic syndrome with various causes, paraneoplastic nephropathy, renal damage associated with multiple myeloma or fibrosis in which it may be indicative or correlate with loss or decline of renal function. The invention may further be applied to urine samples that have been obtained from patients with organ transplantation, more particularly kidney transplantation, as an early marker for rejection of the transplanted organ.

In one particularly advantageous embodiment, the urine sample provided in step a) is a sample collected from such a patient/individual—and in particular from a diabetes patient—who does not or not yet show any sign(s) of microalbuminuria. Usually, this means that the urine sample used in step a) will have an overall protein content expressed as albumin/creatine ratio (ACR)—e.g. as measured by standard methods such as turbidimetry, nephelometry or immunodiffusion for albumin/protein combined with determination of creatinine using well known procedures such as the method of Jaffé—of no more than 2.5 g albumin/mmol creatinine for male patients or 3.5 g/mmol for female patients. Alternatively or in addition the albumin excretion rate can be determined in this case this rate should be below 20 or 30 mg/24 h for male or female patients respectively. As mentioned above, in this embodiment, the method of the invention may be used with advantage to provide a diagnostic and/or prognostic parameter for early kidney damage or the risk thereof, even before any such damage has progressed to such a stage that microalbuminuria already occurs.

Furthermore, as already mentioned above, the invention may be applied to detect early changes in the peritoneal membrane as occurring as complication in CAPD. For this application of the invention, again a urine sample may be used, i.e. in the manner described above. However, as such patients may provide very little or no urine, this aspect of the invention preferably involves the use of a dialysate fluid.

Accordingly, the invention also relates to a method for determining whether (a sample of) a dialysate fluid has been obtained from a subject suffering from (a disorder leading to) remodelling of the peritoneal membrane, said method comprising the steps of:

a) providing at least one sample of dialysate fluid from said subject;
b) determining in said at least one sample of dialysate fluid the presence and/or the level of at least one proteolytic enzyme;

and optionally comprising the further step of:

c) comparing one or more of the values determined in step b) with at least one reference value or reference sample.

In particular, in this aspect of the invention, the (sample of) dialysate fluid will have been obtained from a patient that undergoes (or has undergone) dialysis, and in particular continuous ambulatory peritoneal dialysis (CAPD).

The at least one proteolytic enzyme/protease determined in step b) is preferably a protease involved in vascular remodelling. For instance, in the invention, one or more proteases may be determined that are selected from the group consisting of (matrix) metalloproteases and/or enzymes related to (matrix) metalloproteases. These include, but are not limited to, the proteases schematically shown in FIG. 2, e.g.:

matrix metalloproteases ("MMPs") such as MMP-1, MMP-2, MMP-3, MMP-7, MMP-8, MMP-9, MMP-10, MMP-11, MMP-12, MMP-13; the so-called "MT-MMPs" (e.g. MMP-14 to MMP-17); as well as MMP-18 and MMP-19-MMP-23; and/or proteases related to MMPs such as ADAMs (e.g. ADAM-1 to ADAM-30) or ADAM-TS (e.g. ADAM-TS 1 to ADAM-TS 7);

or any combination thereof.

Other suitable proteases will be clear to the skilled person based upon the disclosure herein, also based upon the art relating to the above and similar proteases (vide for instance Massova et al., Primakoff et al. and Tang and Hong, supra). It is also envisaged that these may include proteases which are only discovered after the priority date of the present application, e.g. based inter alia upon the teaching of the present application.

Preferably, in the method of the invention, the presence and/or the level(s) of at least one of the proteases MMP-1, MMP-2, MMP-8, MMP-9, MMP-13 and/or MMP-14 is determined, and in particular the presence and/or the level(s) of MMP-2 and/or MMP-9; optionally in combination with the presence and/or the levels of one or more of further proteolytic enzymes, and in particular one or more of the further proteases mentioned above.

Even more preferably, the combination of proteases MMP-2 and MMP-9 is determined; again optionally in combination with the presence and/or the levels of one or more of further proteolytic enzymes, and in particular one or more of the further proteases mentioned above.

Also, instead of the presence and/or the levels of one or more of the entire proteases mentioned above, the presence and/or the levels in a urine sample of one or more parts or fragments of such proteases may be determined. These may for instance be parts or fragments that may be considered representative for the presence of the corresponding protease and/or parts or fragments that are (also) indicative of kidney damage as described herein. In particular, these may be (soluble) fragments of normally insoluble, membrane bound, enzymes which are still recognizable either by remaining enzymatic activity or antigenic determinants. Such fragments and the determination thereof should be considered incorporated within the terms "proteolytic enzyme" or "protease" as used herein.

Also, in step b), besides the presence and/or the levels of the one or more of the proteases mentioned above, one or more other parameters of the urine sample may be determined, so as to provide additional information to the clinician. These further parameters may for instance include the presence and/or extent of microalbuminuria; the presence and/or the level(s) of glucose/sugars, or the determination of the presence of erythrocytes, leukocytes, bacteria, paraproteins, etc.

In the invention, when two or more proteases are to be determined, these may be determined in the same sample—which for this purpose may be divided into several parts or fractions—or in different samples. Accordingly, the urine sample of step a) may be a single sample (or a part or fraction thereof) or may be a sample from a set of samples collected from a patient, e.g. essentially simultaneously, for instance on the same day, in the same week and/or at the same clinical stage. It is also encompassed in the scope of the invention that initially only one or a limited number of the proteases mentioned above are determined, and that subsequently one or more further proteases are determined, for instance to confirm the results of the initial determination and/or to provide additional information.

The one or more value(s) obtained in step b) may also be compared to one or more reference values. These may for instance be values obtained from other samples of the same patient/individual (e.g. values obtained from samples collected earlier from the patient); values obtained using one or more reference samples obtained from other patients or individuals (e.g. healthy individuals, individuals with kidney damage with or without albuminuria, and/or patients with diabetes); values obtained through clinical practice or experience; and/or (average) values obtained from one or more groups of patients/individuals, for instance using statistical analysis. The latter may for instance be generated or compiled over time using the method of the invention; it is however also envisaged that after the priority date of the present application, these or other reference values will become available as part of a manual and/or in the scientific literature.

Usually, any such reference value(s) will be—or will have been—determined by the same technique—e.g. using the same assay—as is used to determine the levels of the proteases in the sample of step a); although the invention in its broadest sense is not limited thereto.

The levels of the proteases in a given urine sample may be determined in any manner known per se, including but not limited to:

1) assay techniques involving conversion of natural or artificial substrates followed by a physical separation method such as HPLC;
2) assay techniques involving conversion of labelled natural or artificial substrate followed by measurement of the released (radioactive) label;
3) assay techniques involving conversion of artificial fluorogenic or chromogenic substrate.
4) assay techniques involving zymographic detection in substrate-containing gels;
5) assay techniques involving conversion of modified pro-enzyme substrate, in combination with immuno-capture;
6) assay techniques involving detection of antigen by immunological assay such as ELISA. or any combination thereof.

These methods may be carried out in a manner known per se, for instance as described in the prior art mentioned above, in WO 97/41441, in EP 0 691 409, as well as in D. E. Kleiner and W. G. Stetlerstevenson, Anal. Biochem. 218, 315-319 (1994). The method disclosed in EP 0 691 409 is particularly preferred.

Kits for determining the proteases may also be commercially available. For instance. for methods 2) to 6) mentioned above, kits are commercially available from Roche Diagnostics, Calbiochem, Novagen and Amersham Pharmacia Biotech (for both method 5 and method 6).

Thus, the assay(s) may also be carried out essentially according to the instructions provided with these kits.

Preferably, an immunological method such as method 6 mentioned above and/or a functional method such as methods 1-5 mentioned above is used.

Most preferably, of the above methods 1) to 6), method 5) is used, as methods 1) to 3) may be less or even non-specific; methods 1), 2) and 4) are generally laborious and not useable for large numbers of samples; and method 6) does not measure activity. Method 5) is also described in more detail in EP 0 691 409.

Generally, each protease will be determined using a separate assay specific for said protease (e.g. as described below). However, it is also encompassed in the invention to use assays that can determine the presence and/or the levels of two or more proteases, e.g. combined and/or simultaneously. Also, each separate assay will be usually be carried out on a separate sample or a separate part or fraction of a sample; although again the invention in its broadest sense is not limited thereto.

In the invention, a sample obtained from a patient suffering from renal damage or a renal disorder will show the presence of one or more of the proteases indicated above.

In particular, in the invention, a sample obtained from a patient suffering from renal damage or a renal disorder will show, compared to a sample obtained from a healthy individual, increased levels of one or more of one or more of the proteases indicated above, e.g. increased from a value of essentially zero to a measurable/detectable amount, and/or increased by at least a factor 2, in particular by a factor 5 or higher.

More in particular, in the invention, a sample obtained from a patient suffering from renal damage or a renal disorder will show one or more of the following:

the presence of MMP-2, and in particular the presence of increased levels of MMP-2 compared to a sample obtained from a healthy individual. For instance, the sample may show a urinary MMP activity—e.g. as determined by method 5)—above of 200 U/mmol creatinine;

the presence of MMP-9, and in particular the presence of increased levels of MMP-9 compared to a sample obtained from a healthy individual. For instance, the sample may show a urinary MMP activity—e.g. as determined by method 5)—above of 200 U·mmol creatinine;

the simultaneous presence of both MMP-2 and MMP-9 and in particular the simultaneous presence of increased levels of these enzymes as compared to a sample obtained from a healthy individual.

Thus, the method of the invention may be used to determine whether a given urine sample has been obtained from a patient suffering from kidney damage or not; and thus may provide valuable information on the clinical status of said patient.

In addition, the method of the invention may for instance be used—after it has been established (e.g. by the method of the invention or any other method) that some (early) kidney damage has already occurred—to predict and/or to follow the further course of such damage.

It is even envisaged that the method of the invention may even be used to determine whether and/or when an individual—e.g. a healthy individual but in particular a diabetes patient—is at (further increased) risk of developing renal damage. It may even be that the presence and/or the levels of different proteases, and/or the ratio(s) of these levels, may be indicative for different renal disorders and/or for different forms of renal damage; for different causes of renal damage; and/or for different clinical stages of renal disorders or for a specific extent of renal damage.

Thus, the method of the invention provides the clinician with a convenient yet very reliable and powerful tool for diagnosing, predicting and/or following renal disorders, renal damage and/or the clinical course thereof, in particular in patients that are at (increased) risk thereof. These may include but are not limited to diabetes patients; and more generally comprise patients of any disease and/or disorder that may cause and/or lead to kidney damage (also as a complication of said disease and/or disorder). For instance, the results obtained using the method of the invention may lead the clinical to prescribe treatment or to change or modify a treatment already prescribed.

Also, method of the invention may be used in diagnosing, predicting and/or following (early) kidney renal in subjects that are undergoing treatment with any medication that may cause kidney damage (e.g. as a side-effect of said medication). Again, the results obtained using the method of the invention may lead the clinical to change or modify said treatment.

It is also envisaged that, besides the above clinical application(s), the method of the invention may also find applications in other areas, for instance to determine whether a new drug may cause kidney damage (e.g. as a side-effect) and/or in studying the effects of drugs that are intended to prevent and/or counteract kidney disorders and/or kidney damage, e.g. damage caused by dysregulation of remodelling processes. Thus, it is expected that the method of the invention may also be useful for research purposes, for instance in drug discovery, drug testing and/or drug development.

DETAILED DESCRIPTION OF THE INVENTION

The invention relates to determine the level of a protease or a number of proteases in urine as a diagnostic, prognostic or otherwise medically interesting marker for the occurrence, progression, therapeutic effect or otherwise medically interesting fact of diseases possibly leading to vascular complications in general and more specifically to damage to the (micro) vasculature of the kidney resulting in partial, gradual, acute or total loss of function of this organ. More particular the present invention relates to (very) early detection of processes eventually leading to such a damage. Ideally this detection is early enough to be able to prevent serious damage by timely starting a suitable therapy or preventive strategy.

The phrase "determining the level of a protease or a number of proteases" means both qualitative analysis i.e. determining the presence of the protease or proteases above a certain well chosen threshold level and quantitative analysis i.e. determining the level of proteases belonging to the family of matrix-metalloproteases (MMPs), ADAMs or ADAMTSs (table I). This is not limited to only those proteases since virtually any protease involved in vascular remodelling might serve the purpose in certain cases, conceivably dependent on the specific pathology leading to the kidney damage. Particularly interesting are the various MMPs (table 2), enzymes known to be involved in local tissue remodelling and degradation.

Detection or quantification of the particular protease or proteases can be based on its enzymatic activity, or alternatively based on detection of the antigen. For both ways of detection general or specific methodology is available or can be devised based on currently known technology (table 3). It is conceivable that detection or measurement of a combination of two or more proteolytic enzymes is a way to obtain sufficient reliability. The method focuses on urine as a biological fluid since in urine of healthy control subjects hardly any proteolytic enzyme can be detected and urine is currently used as a biological fluid for diagnostic and other medical purposes in e.g. the field of diabetes and consequently fits well with current medical and clinical chemistry practice.

Possible applications of the present invention include, but are not limited to:
  (early) diagnosis of renal damage resulting from diabetes or other diseases, enabling the start of therapeutic or preventive actions before renal failure occurs;
  monitoring the effect of therapeutic or preventive intervention;
  prediction of the most likely progression of the disease related renal damage; more specifically damage to the microvasculature of the kidney frequently occurs as a complication of diabetes mellitus but can also have other causes.

Early detection is important to prevent serious damage leading to kidney failure. At present the determination of trace quantities of albumin in the urine (microalbuminuria) is the established method to detect renal damage. A method that would give an earlier warning for still initial and possibly reversible renal damage would be desirable.

Thus, the invention provides a non-invasive method for facilitating diagnosis or prognosis of kidney damage in a subject comprising obtaining a sample of urine from said subject and detecting a proteolytic enzyme in said sample thereby facilitating the diagnosis of the subject for conditions leading to kidney damage, in which the proteases and the manner in which these proteases are determined are as mentioned above. The condition leading to kidney damage may in particular be diabetes, more in particular be diabetes type 1 and/or diabetes type 2.

In another aspect, the invention also relates to the use of an assay for determining the presence and/or the level of at least one protease as mentioned above, in determining whether a urine sample has been derived from a patient suffering from a kidney disorder and/or kidney damage, and in particular from kidney damage caused by diabetes, in which said assay is used to determine the presence and/or the levels of said at least one protease in said urine sample. In particular, as mentioned above, the urine sample is a urine sample obtained from a patient that is (judged to be) at risk of—and/or that suffers from and/or is suspected to suffer from—such kidney damage, and/or may be a urine sample obtained from a patient suffering from diabetes.

In another aspect, the invention relates to the use of means for determining the presence and/or levels of at least one proteolytic enzyme, in a method as described above. Such means may for instance be means for carrying out one of the assay techniques referred to above, such as the methods 1) to 6). Usually said means will be (provided to the end-user) in the form of a kit, and such kits are known in the art and may be commercially available.

DESCRIPTION OF THE FIGURES

FIG. 1 is a graph/diagram showing total active and activatable MMP-2 in 24-h urine collections of controls and patients, as determined with a commercially available immunocapture assay kit for MMP-2 activity (Amersham Pharma Biotech RPN 2631) and as expressed as units per mmol creatinine;

FIG. 2 is a graph/diagram showing total active and activatable MMP-9 in 24-h urine collections of controls and patients, as determined with a commercially available immunocapture assay kit for MMP-9 activity (Amersham Pharma Biotech RPN 2630) and as expressed as units per mmol creatinine;

FIG. 3 is a graph/diagram showing total MMP-9 activity in urine of patients with rheumatoid arthritis before and after treatment with a drug supposed to inhibit cartilage degradation, as determined with a commercially available immunocapture assay kit for MMP-9 activity (Amersham Pharma Biotech RPN 2630) and as expressed as units per mmol creatinine.

FIG. 4 is a graph/diagram showing total MMP-2 and MMP-9 activity in the urine of diabetes patients with microalbuminuria.

FIG. 5 is a graph/diagram showing total MMP-2 and MMP-9 activity in the urine of normal albuminuric diabetes patients.

Activities were measured with commercially available immuno capture kits (Amersham Pharmacia Biotech RPN 2631 and RPN 2630.

EXAMPLES

Example I

Measurement of MMP-2 Antigen in Serum of Healthy Controls and Diabetic Patients with and without Albuminuria The level of matrix-metalloprotease-2 (MMP-2) antigen in serum of healthy control (n=9) and patients with type I diabetes with (n=16) and without (n=140) albuminuria was determined using a commercially available ELISA (Amersham Pharmacia Biotech RPN 2617 kit).

No significant differences in levels between the various groups were found: control 547±38 ng/ml, diabetes patients with albuminuria 608±42 ng/ml and diabetes patients without albuminuria 612±44 ng/ml (mean±SEM).

Example II

Measurement of MMP-9 Antigen in Serum of Healthy Controls and Diabetic Patients with and without Albuminuria The level of matrix-metalloproteases-9 (MMP-9) in serum of healthy controls (n=9) and patients with type I diabetes with (n=16) and without (n=14) albuminuria was determined using a commercially available ELISA (Amersham Pharmacia Biotech RPN 2614 kit). Patient serum MMP-9 levels were significantly increased versus controls (508±38 ng/ml vs. 159±17 ng/ml; $p<0.001$). No difference was observed between patients with and without albuminuria.

Example III

Inactive Pro-Forms of MMPs are Converted to Active Forms by Treatment with Amino-Phenyl-Mercuric-Acetate (APMA)

A MMP containing sample after immunocapture is incubated with 0.5 mM APMA at 37 C for 2 h (MMP-9) or 0.5 h (MMP-2) as described in the instructions of the manufacturer of the kits. Measurement without APMA treatment gives active MMP present in the sample, whereas measurement after APMA treatment gives active and activatable pro-enzyme in the sample.

Example IV

Measurement of MMP-2 Activity in Urine of Healthy Controls and Diabetic Patients with and without Albuminuria Total Active and activatable MMP-2 was determined in 24-h urine collections of controls and patients with a commercially available immunocapture assay kit for MMP-2 activity (Amersham Pharma Biotech RPN 2631) and expressed as units per mmol creatinine. MMP-2 level in controls was non detectable (<0.1 units/mmol creatinine), whereas urine of diabetic patients with albuminuria had significantly increased levels as compared with patients without albuminuria (median 458) (range 0-10959) versus 0 (range 0-3026) units/mmol creatinine ($p<0.003$ Mann Whitney U test). (see FIG. 1)

Example V

Measurement of MMP-9 Activity in Urine of Healthy Controls and Diabetic Patients with and without Albuminuria Total and activatable MMP-9 levels were determined in 24 h urine collections of healthy controls and diabetic patients using a commercially available immunocapture assay kit for MMP-9 activity (Amersham Pharmacia Biotech RPN 2630). Total (active+activatable) MMP-9 was not detectable in urine of normals, whereas it was clearly increased in urine of diabetic patients with albuminuria versus patients without albuminuria (median 964 (range 0-26129) versus 0 (range 0-3519) units/mmol creatinine). (See FIG. 2)

Example VI

Measurement of Total MMP-9 Activity in Urine of Patients with Rheumatoid Arthritis Before and after Treatment with a Drug Supposed to Inhibit Cartilage Degradation MMP-9 activity was measured with the method of example V. (See FIG. 3).

Example VII

Measurement of Total MMP-2 and MMP-9 Activity in Urine of Patients with Microalbuminuria or Normoalbuminuric Patients In patients with microalbuminuria at least one of the two measured MMPs is detectable (see FIG. 4), whereas in normal albuminuric patients neither of the two or sporadically one of the two MMPs measured is detectable (see FIG. 5).

The invention claimed is:

1. A method for determining whether subject having Type II diabetes has a kidney disorder, the method comprising the steps of:
   a) providing a urine sample from the subject having Type II diabetes;
   b) determining in the urine sample the level of matrix metalloproteinase-8 (MMP-8); and
   c) comparing one or more of the values determined in step b) with a reference value or reference sample from a healthy individual; and
   d) determining whether the subject has a kidney disorder based on the presence of increased levels of MMP-8 in the urine compared to the reference values or reference sample.

2. The method according to claim 1, wherein the subject does not show any sign of microalbuminuria indicated by at least one of overall protein content of said urine sample and albumin excretion rate, said overall protein content of said urine sample indicates no sign of microalbuminuria for no more than 2.5 g albumin/mmol creatinine for a male subject and no more than 3.5 g albumin/mmol creatinine for a female subject, and said albumin excretion rate indicates no sign of microalbuminuria at a rate below 20 mg/24 h for a male subject or at a rate below 30 mg/24 h for a female subject.

* * * * *